US005645541A

United States Patent [19]
Bouser

[11] Patent Number: 5,645,541
[45] Date of Patent: Jul. 8, 1997

[54] URINAL DEVICE

[76] Inventor: Richard E. Bouser, 655 Brookfield Ave., Masury, Ohio 44438

[21] Appl. No.: 630,845

[22] Filed: Apr. 11, 1996

Related U.S. Application Data

[63] Continuation-in-part of Ser. No. 278,811, Jul. 22, 1994, Pat. No. 5,520,671.

[51] Int. Cl.$^6$ ........................................ A61F 5/44
[52] U.S. Cl. ........................ 604/353; 604/349; 604/351
[58] Field of Search ...................... 604/349–353, 604/355

[56] References Cited

U.S. PATENT DOCUMENTS

| | | | |
|---|---|---|---|
| 1,423,537 | 7/1922 | Mueller | 604/353 |
| 2,484,356 | 10/1949 | Ribeiro et al. | 604/353 |
| 2,840,079 | 6/1958 | Conway et al. | 604/350 |
| 3,526,227 | 9/1970 | Appelbaum | 604/350 |
| 4,387,726 | 6/1983 | Denard | 604/350 |
| 4,850,986 | 7/1989 | Temple | 604/349 |
| 5,195,997 | 3/1993 | Carns | 604/353 |
| 5,423,785 | 6/1995 | Hart | 604/353 |
| 5,478,334 | 12/1995 | Berstein | 604/353 |
| 5,520,671 | 5/1996 | Bouser | 604/353 |

FOREIGN PATENT DOCUMENTS

| | | | |
|---|---|---|---|
| 674158 | 4/1939 | Germany | 604/349 |

*Primary Examiner*—Mark O. Polutta

[57] ABSTRACT

A urinal device is disclosed for the reception therein of a user's penis. The device includes a support worn by the user for supporting the device relative to the user. A collar is secured to the support for the reception therein of the user's penis. The arrangement is such that in use of the device, the user's penis is inserted through the collar. The collar has a first and a second end. A flexible tubular portion is provided for sealing the device relative to the user's penis, the tubular portion having a first and second extremity. The first extremity engages the first end of the collar and the second extremity sealingly cooperates with the user's penis. A collection device sealingly cooperates with the second end of the collar, the arrangement being such that in use of the device, the user's penis is sealingly supported by the tubular portion so that the user's penis is disposed within the collar.

9 Claims, 5 Drawing Sheets

URINAL DEVICE

CROSS REFERENCE TO RELATED APPLICATION.

The present application is a continuation in part application of application U.S. Ser. No. 08/278,811 now U.S. Pat. No. 5,520,671 filed Jul. 22, 1994. All the disclosure of the aforementioned application is incorporated herein by reference.

FIELD OF THE INVENTION

The present invention relates to a urinal device. More particularly, the present invention relates to a device for the reception therein of a user's penis.

BACKGROUND OF THE INVENTION

Many devices have been manufactured for use by a patient suffering from incontinence. Most of the aforementioned devices include a collection bag for collecting the patient's urine and means for connecting the bag to the body of the user.

In the case of male patients, the prior art urinal devices usually include a connector arrangement through which the user's penis is inserted and a flexible collar which is intended to seal against the user's penis in order to inhibit leakage of urine therepast.

However, the aforementioned prior art devices do not consistently provide a waterproof seal. Furthermore, a patient having undergone surgery and suffering from the condition of retracting penis is presented with a serious problem with regard to sealing the unit against leakage.

More particularly, external urinal devices of the aforementioned type have been especially recommended for patients suffering from occasional or complete urinary incontinence. However, in operation such devices have not always been entirely satisfactory.

On the other hand, the device according to the present invention offers comfortable freedom of movement for the user without any embarrassment that would be occasioned by leakage from the unit.

The device according to the present invention is particularly useful for men suffering from the medical condition known as "retracting penis". The aforementioned prior art units have been inadequate in overcoming the problem of sealing and securing such device to the user thereof without subsequent leakage.

Additionally, the prior art arrangements suffer from the drawback of causing irritation to the skin. Also, such prior devices have caused a restriction of movement of the user.

The device according to the present invention is easily fitted to a male patient including those suffering from the condition known as retracting penis.

The device according to the present invention has a distinct advantage over the prior art arrangements in that such prior art devices require special clamps and the like in order to provide adequate sealing.

The device according to the present invention includes a collection device which is either directly connected to a collar or alternatively is connected to the collar by means of latex tubing. An adapter connects the tubing to a leg bag or the like depending on the level of the patient's incontinence.

The device according to the present invention includes a latex sheath which may be hygienically cleaned with soap and water.

Ideally, the patient would be provided with two units, one unit would be worn by the patient while the other unit is being washed and dried.

Therefore, it is a primary objective of the present invention to provide a urinary device that overcomes the aforementioned inadequacies of the prior art devices and which makes a considerable contribution to the medical art.

Other objects and advantages of the present invention will be readily apparent to those skilled in the art by reference to the detailed description contained hereinafter taken in conjunction with the annexed drawings.

SUMMARY OF THE INVENTION

The present invention relates to a urinal device for the reception therein of a user's penis. The device includes a support worn by the user for supporting the device relative to the user. A collar is secured to the support for the reception therein of the user's penis. The arrangement is such that in use of the device, the user's penis is inserted through the collar. The collar has a first and a second end. A flexible tubular portion is provided for sealing the device relative to the user's penis, the tubular portion having a first and second extremity. The first extremity sealingly engages the first end of the collar and the second extremity sealingly co-operates with the user's penis. A collection device sealingly co-operates with the second end of the collar. The arrangement is such that, in use of the device, the user's penis is sealingly supported by the tubular portion so that the user's penis is disposed within the collar.

In a more specific embodiment of the present invention, the support means includes a waist band having a first and a second end. Fastening means are secured to the band for fastening the ends thereof together.

The support means is preferably fabricated from cloth and the collar means is fabricated from a of plastics material.

In a Specific embodiment of the present invention, the collar is of polyvinylchloride and has a length within the range 2 to 6 inches and an outside diameter within the range 2 to 3 inches. The inside diameter is within the range 1.25 to 1.75 inches.

Additionally, the collar means includes a first portion which extends from the first end of the collar means. The first portion defines an annular groove which cooperates with the first extremity of the tubular means for sealing the tubular means relative to the collar means.

The second portion extends from the first portion to the second end of the collar means. The second portion defines an annular depression for sealingly engaging the collection means.

The second portion has a lesser outside diameter than an outside diameter of the first portion.

Additionally, the urinal device includes an O-ring which removably cooperates with the annular depression for removably attaching the collection means to the second end of the collar means.

In a preferred embodiment of the present invention, the tubular means is of latex material and is fabricated from a condom which defines the first and the second extremity. The arrangement is such that the first extremity cooperates with and is stretched over the first end of the collar means. The second extremity is cut off to a size which sealingly cooperates with the user's penis thereby preventing leakage therepast in the event that the user thereof has undergone surgery resulting in the condition known as "retracting penis."

Furthermore, the collection means includes a tubular sleeve which is connected to the second end of the collar means. A collection bag is connected to the tubular sleeve such that the tubular sleeve is disposed between the collar means and the bag.

The collection bag is fabricated from a latex material and the tubular sleeve has an open end which is removably stretched over the second end of the collar means.

More specifically, the present invention relates to a urinal device for the reception therein of a user's penis, the device comprising:

support means worn by the user for supporting the device relative to the user;

collar means secured to the support means for the reception therein of the user's penis, the collar means having a length of at least 2 inches, the collar means having a first and a second portion, the first portion having an outside diameter which is greater than an outside diameter of the second portion, the first and second portions being disposed on opposite sides of the support means with the first portion being disposed nearest to the user and between the user and the support means for supporting therein the user's penis, the arrangement being such that in use of the device, the user's penis is inserted through the collar means, the collar means having a first and second end the arrangement being such that in use of the device, any tendency for the user's penis to retract away from the first portion is inhibited thereby preventing leakage therepast;

flexible tubular means for sealing the device relative to the user's penis, the tubular means having a first and second extremity, the first extremity sealingly engaging the first end of the collar means, the second extremity sealingly cooperating with the user's penis;

collection means sealingly cooperating with the second end of the collar means, the arrangement being such that in use of the device, the user's penis is sealingly supported by the tubular means so that the user's penis is disposed within the collar means;

the collection means including:

a tubular sleeve connected to the second end of the collar means;

a collection bag connected to the tubular sleeve such that the tubular sleeve is disposed between the collar means and the bag; and the tubular sleeve being fabricated from latex material.

In a more specific modification of the present invention the collar means is of "L" shaped configuration.

Furthermore, the first portion is of open ended cylindrical configuration and the second portion extends from the first portion and is disposed approximately 90 degrees thereto for permitting the orientation of the collar means in any position thereof within the range 0–360 degrees relative to the user's penis so that the user thereof is able to sleep on either of the user's sides or on the user's back.

Additionally, in a more specific configuration, the second portion is rotatably received within the first portion for permitting rotation of the second portion relative to the first portion.

More specifically, the first portion has a length of approximately 1.75 inches so that in use of the device, the first portion is disposed between the support means and the user's stomach such that the support means urges the first portion towards the user's stomach thereby inhibiting any tendency of the user's penis from retracting from within the first portion.

In another embodiment of the present invention, the collection means includes:

a tubular collection sleeve having a proximal and a distal end, the proximal end being sealingly secured to the second end of the collar means;

a valve disposed within the distal end for controllably draining the collection means.

In another embodiment, the first and second portions are both of open ended cylindrical configuration, the portions being coaxial.

Many modifications and variations of the present invention will be readily apparent to those skilled in the art by a consideration of the detailed description contained hereinafter taken in conjunction with the annexed drawings. However, such modifications and variations fall within the spirit and scope of the present invention as defined by the appended claims.

BRIEF DESCRIPTION OF THE DRAWINGS.

Similar reference characters refer to similar parts throughout the various views of the drawings.

DETAILED DESCRIPTION OF THE DRAWINGS.

Figures 1, 3:
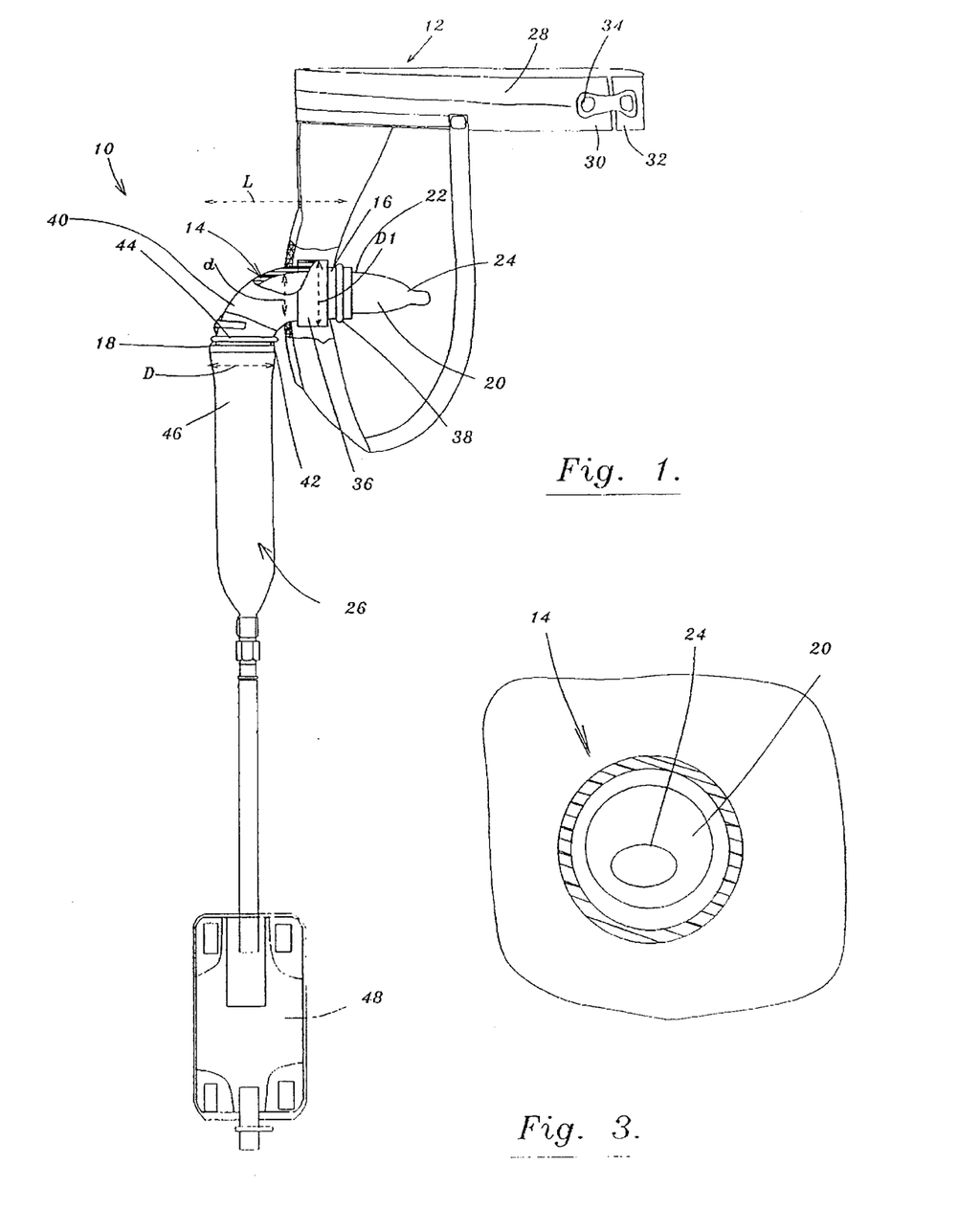
FIG. 1 is a side elevational view partially in sections showing a urinal device according to the present invention;.
FIG. 3 is a sectional view taken on the line 3—3 of FIG. 2.
Figure 2:
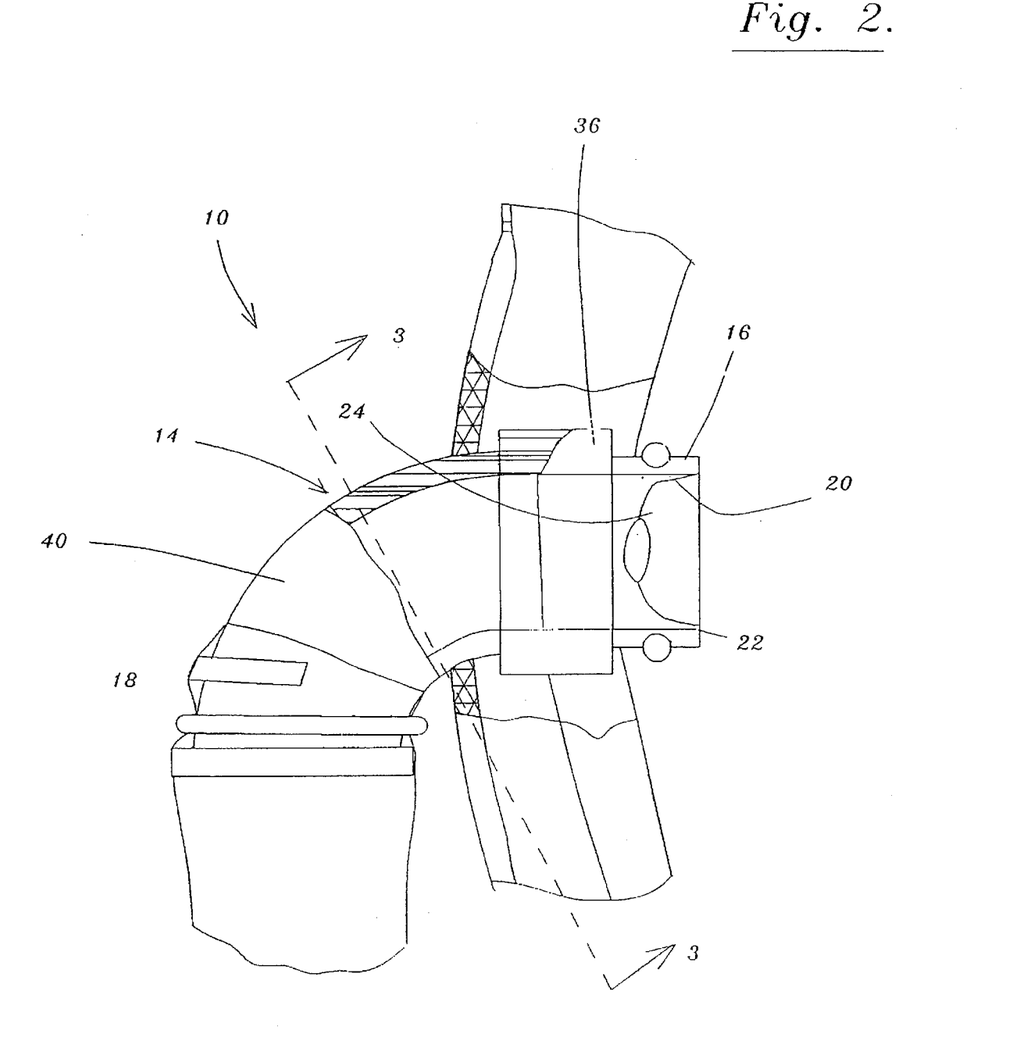
FIG. 2 is an enlarged view partially in section of the collar means of the urinal device shown in FIG. 1.

FIGS. 1–3 show a urinal device generally designated 10 for the reception therein of a user's penis. The device includes support means generally designated 12 worn by the user for supporting the device relative to the user.

A collar means generally designated 14 is secured to the support means 12 for the reception therein of the user's penis, the arrangement being such that in use of the device 10, the user's penis is inserted through the collar means 14, the collar means 14 having a first and a second end 16 and 18 respectively.

In operation of the device 10 according to the present invention, the patient steps into the belted support 12 and pulls the support means 12 up over the user's hips. A flexible tubular means 20 or latex sheath is adjusted over the penis so that it rests securely where the penis joins the stomach.

The penis is adjusted inside the urinal sheath 20 so that the head of the penis protrudes through the front of the narrowest part of the sheath 20. Prior to wearing the device, the user trims the sheath 20 to the correct size to fit the user. Petroleum jelly or other ointment recommended by a physician may be beneficial in order to successfully fit the unit.

The device 10 works by preventing a back flow of urine. More particularly, the flexible tubular means 20 having been cut to the correct size seals against the walls of the penis to provide a seal therewith in order to prevent backflow of urine.

The support means 12 is made from a combination of fabrics to ensure breath ability while the tubular means 20 is of latex.

More specifically, the flexible tubular means 20 for sealing the device 10 relative to the user's penis includes a first and second extremity 22 and 24 respectively. The first extremity 22 sealingly engages the first end 16 of the collar means 14. The second extremity 24 is cut to size as shown in FIG. 2 so that the second extremity 24 sealingly cooperates with the user's penis.

The device 10 also includes a collection means generally designated 26 which sealingly cooperates with the second end 18 of the collar means 14. The arrangement is such that in use of the device 10, the user's penis is sealingly supported by the tubular means 20 so that the user's penis is disposed within the collar means 14.

The support means 12 also includes a waist band 28 having a first and second end 30 and 32 and fastening means 34 secured to the waist band 28 for fastening the ends 30 and 32 together.

In a preferred embodiment of the present invention the support means 12 is fabricated from cloth.

The collar means 14 is of plastics material and is preferably made from PVC (polyvinylchloride).

The collar means 14 has a length L within the range 2 to 6 inches and an outside diameter D within the range 2 to 3 inches and an inside diameter d within a range 1.25 to 1.75 inches.

The collar means 14 collar means includes a first portion 36 extending from the first end 16 of the collar means 14. The first portion 36 defines an annular groove 38 which cooperates with the first extremity 22 of the tubular means 20 for sealing the tubular means 20 relative to the collar means 14.

A second portion 40 extends between the first portion 36 and the second end 18 of the collar means 14. The second portion 40 defines an annular depression 42 for sealingly engaging the collection means 26.

The second portion 40 has a lesser outside diameter D than an outside diameter D1 of the first portion 36.

An O-ring 44 removably cooperates with the annular depression 42 for removably attaching the collection means 26 to the second end 18 of the collar means 14.

The tubular means 20 is of latex material and is preferably fabricated from a condom defining the first and second extremities 22 and 24, the arrangement being such that the first extremity 22 cooperates with and is stretched over the first end 16 of the collar means 14. Prior to the use of the device, the second extremity 24 is cut off to a size which sealingly cooperates with the user's penis thereby preventing leakage therepast in the event that the user thereof has undergone surgery resulting in the condition known as "retracting penis."

The collection means 26 includes a tubular sleeve 46 connected to the second end 18 of the collar means 14.

A collection bag 48 is connected to the tubular sleeve 46 such that the tubular sleeve 46 is disposed between the collar means 14 and the bag 48.

The collection means 26 is fabricated from latex material.

As shown in FIG. 3, Prior to fitting the device, the condom or sheath is cut off approximately half an inch from the first end of the collar means 14. Typically, in order to fit the device, the foreskin is held back off the head of the penis by the cut portion of the condom.

Figures 4, 5:
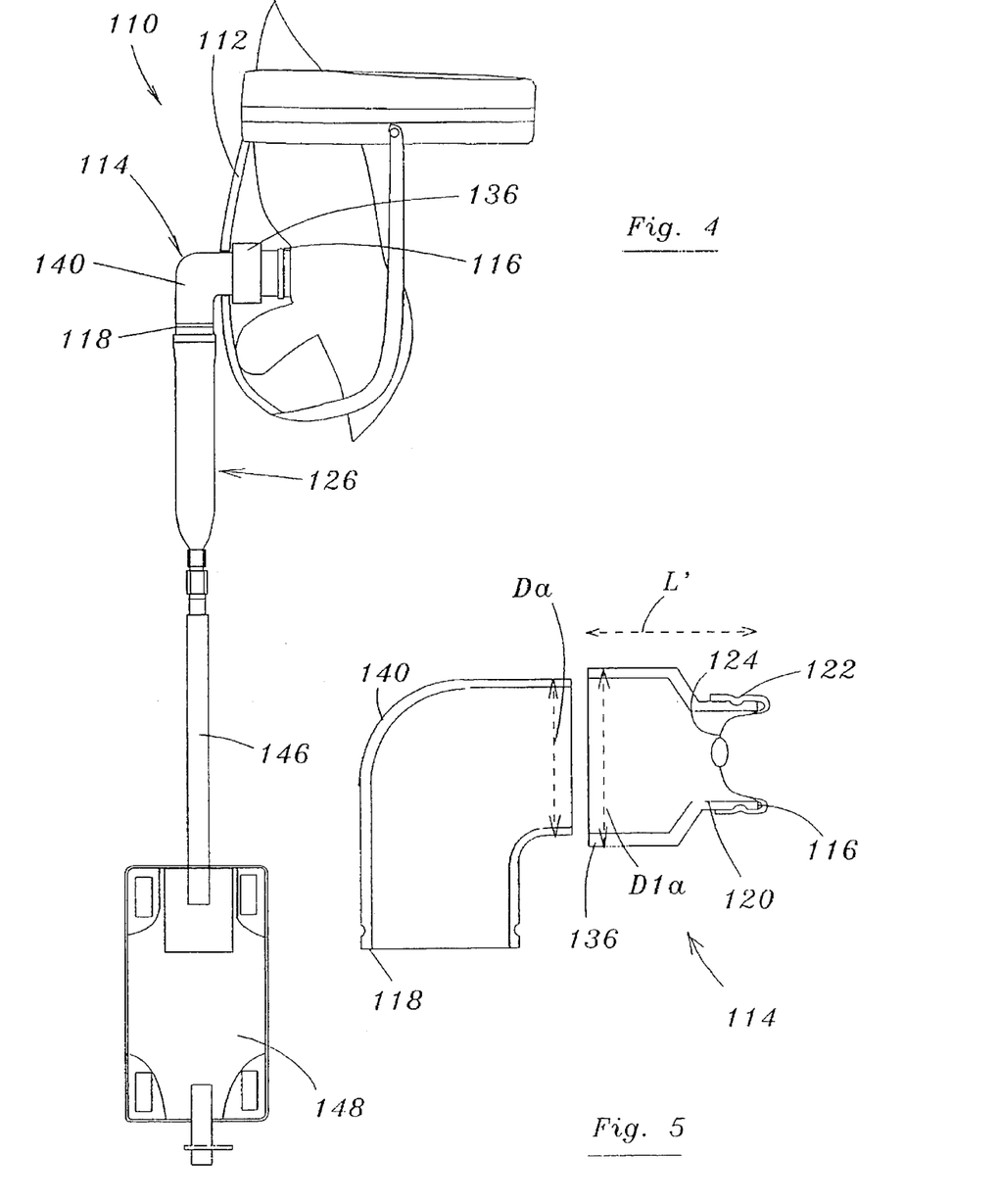
FIG. 4 is a side elevational view of the device according to an alternative embodiment of the present invention.
FIG. 5 is an enlarged view of the device shown in FIG. 4.

FIG. 4 is a side elevational view of a specific embodiment of the present invention. FIG. 4 shows a urinal device 110 for the reception therein of a user's penis. The device 110 includes: support means 112 worn by the user for supporting the device 110 relative to the user; collar means 114 secured to the support means 112 for the reception therein of the user's penis, the collar means 112 having a length of at least 2 inches, the collar means 112 having a first and a second portion 136 and 140 respectively.

FIG. 5 is an enlarged sectional view of the collar means 114 disassembled for clarity. The first portion 136 has an outside diameter D1 a which is greater than an outside diameter Da of the second portion 140. The first and second portions 136 and 140 are disposed on opposite sides of the support means 112 as shown in FIG. 4 with the first portion 136 being disposed nearest to the user and between the user and the support means 112 for supporting therein the user's penis. The arrangement is such that in use of the device 110, the user's penis is inserted through the collar means 114, the collar means 114 having a first and second end 116 and 118 respectively, such that in use of the device, any tendency for the user's penis to retract away from the first portion 136 is inhibited thereby preventing leakage therepast.

The device 110 also includes a flexible tubular means 120 for sealing the device 110 relative to the user's penis, the tubular means 120 having a first and second extremity 122 and 124 respectively. The first extremity 122 sealingly engages the first end 116 of the collar means 114. The second extremity 124 sealingly cooperates with the user's penis.

Collection means 126 sealingly cooperate with the second end 118 of the collar means 114. The arrangement is such that in use of the device, the user's penis is sealingly supported by the tubular means 120 so that the user's penis is disposed within the collar means 114.

The collection means 126 includes:
a tubular sleeve 146 connected to the second end 118 of the collar means 114 and a collection bag 148 connected to the tubular sleeve 146 such that the tubular sleeve 146 is disposed between the collar means 114 and the bag 148.

Additionally, the tubular sleeve 146 is fabricated from latex material.

More specifically, as shown in FIGS. 4 and 5, the collar means 14 is of "L" shaped configuration.

Furthermore, the first portion 136 is of open ended cylindrical configuration and the second portion 140 extends from the first portion 136 and is disposed approximately 90 degrees thereto for permitting the orientation of the collar means 114 in any position thereof within the range 0–360 degrees relative to the user's penis so that the user thereof is able to sleep on either side or on the user's back.

Additionally, as shown in FIG. 5, the second portion 140 is rotatably received within the first portion 136 for permitting rotation of the second portion 140 relative to the first portion 136.

More specifically, the first portion 136 has a length L' of approximately 1.75 inches so that in use of the device, the first portion 136 is disposed between the support means 112 and the user's stomach such that the support means 112 urges the first portion 136 towards the user's stomach thereby inhibiting any tendency of the user's penis from retracting from within the first portion 136.

Figure 6:
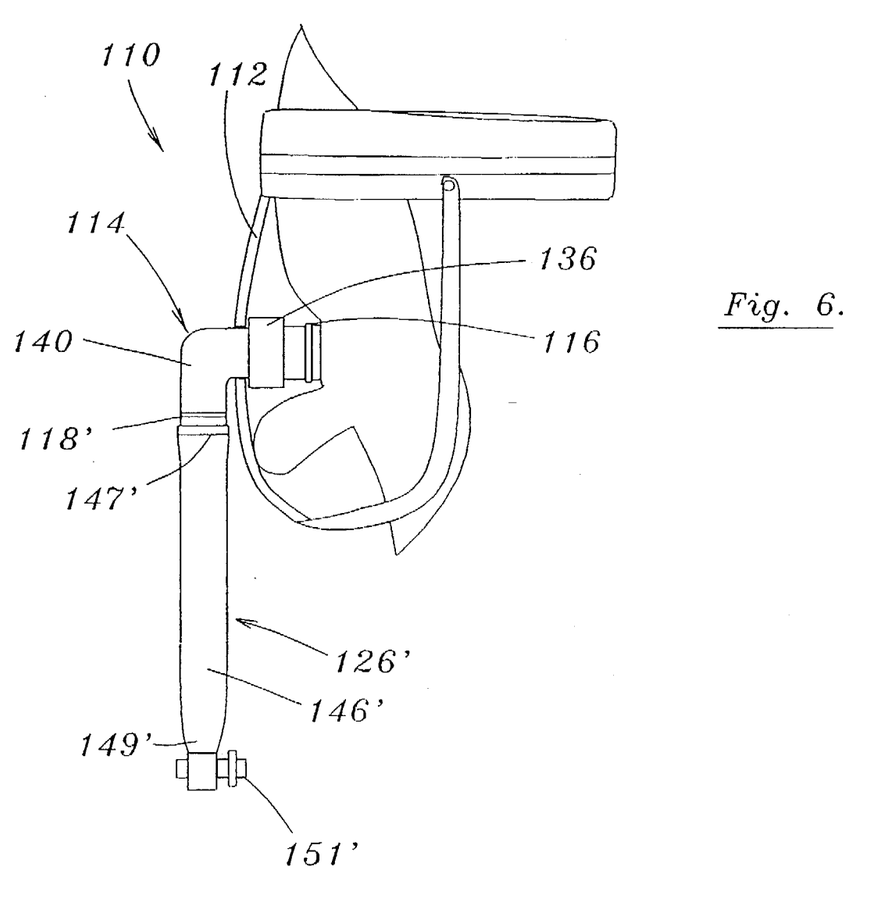
FIG. 6 is a side elevational view of yet another embodiment of the present invention showing the collection means and a drainage valve therefore.

In another embodiment of the present invention as shown in FIG. 6, the collection means 126' includes a tubular collection sleeve 146' having a proximal and a distal end 147' and 149' respectively. The proximal end 147' is sealingly secured to the second end 118' of the collar means 114'.

A valve 151' is disposed within the distal end 149' for controllably draining the collection means 126'.

Figures 7, 8:
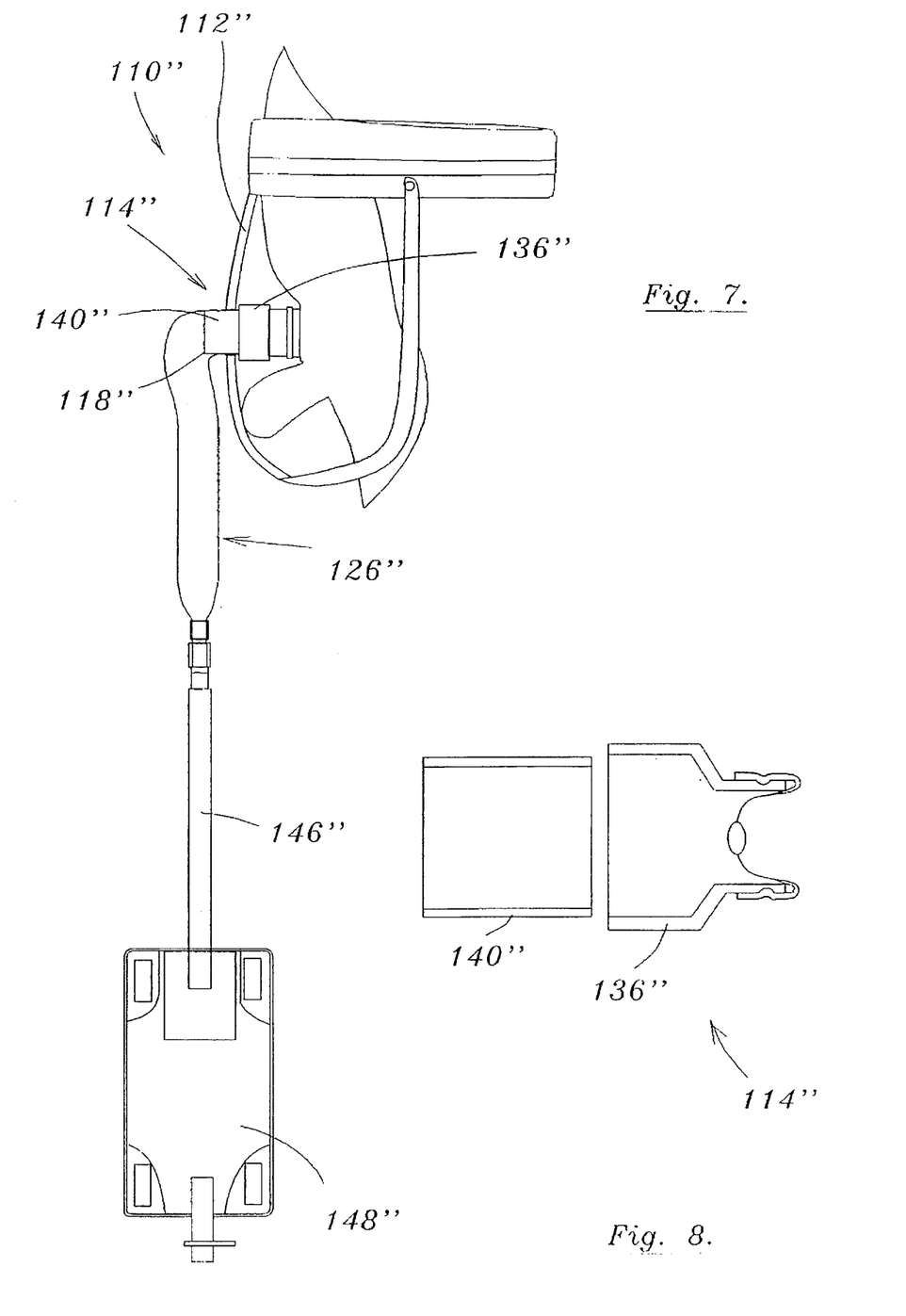
FIG. 7 is a side elevational view of yet another embodiment of the present invention in which the first and second portions of the collar means are coaxial.
FIG. 8 is an enlarged sectional view of the collar means shown in FIG. 7

Additionally, in another embodiment of the present invention as shown in FIGS. 7 and 8, the first and second portions 136" and 140" are both of open ended cylindrical configuration, the portions 136" and 140" being coaxial.

The inventor of the present invention prior to making the aforementioned invention underwent surgery which resulted in the condition known as "retracting penis".

The inventor subsequently went to several pharmacies and consulted with numerous doctors, nurses and ENT professionals and home health care facilities. However, none of the aforementioned specialists could provide a device for overcoming the problem of leakage associated with the aforementioned retracting penis condition.

According to the inventor's experience there was nothing available on the market that could prevent leakage and provide freedom from pain and discomfort.

In the case of the inventor, the inventor underwent prostectomy and was subsequently fitted with a "Cunningham clamp device." Such device involved penis strangulation which resulted in pain and irritation and also did not prevent leakage.

The device according to the present invention reliably seals against any leakage thereby affording the user thereof freedom of movement without the fear of embarrassment. The device according to the present invention may be worn without irritation for considerable periods without any discomfort to the user thereof.

What is claimed is:

1. A urinal device for the reception therein of a user's penis, said device comprising:

collar means for the reception therein of the user's penis said collar means having a length of at least 2 inches, said collar means having a first and a second portion;

support means adapted to be worn by the user for supporting said collar means relative to the user;

said first and second portions being disposed on opposite sides of said support means with said first portion for being disposed nearest to the user and between the user and said support means for supporting therein the user's penis, the arrangement being such that in use of the device, the user's penis is inserted through said collar means, said collar means having a first and second end the arrangement being such that in use of the device, any tendency for the user's penis to retract away from said first portion is inhibited thereby preventing leakage therepast;

flexible tubular means fabricated from latex material for sealing said device relative to the user's penis, said tubular means having a first and second extremity, said first extremity sealingly engaging said first end of said collar means, said second extremity for sealingly cooperating with the user's penis;

collection means sealingly cooperating with said second end of said collar means, the arrangement being such that in use of the device, the user's penis is sealingly supported by said tubular means so that the user's penis is disposed within said collar means;

said collection means including:

a tubular sleeve connected to said second end of said collar means;

a collection bag connected to said tubular sleeve such that said tubular sleeve is disposed between said collar means and said bag; and said tubular sleeve being fabricated from latex material.

2. A urinal device for the reception therein of a user's penis, said device comprising:

collar means for the reception therein of the user's penis said collar means having a length of at least 2 inches, said collar means having a first and a second portion, said first portion having an outside diameter which is greater than an outside diameter of said second portion;

support means adapted to be worn by the user for supporting said collar means;

said first and second portions being disposed on opposite sides of said support means with said first portion for being disposed nearest to the user and between the user and said support means for supporting therein the user's penis, the arrangement being such that in use of the device, the user's penis is inserted through said collar means, said collar means having a first and second end the arrangement being such that in use of the device, any tendency for the user's penis to retract away from said first portion is inhibited thereby preventing leakage therepast;

flexible tubular means for sealing said device relative to the user's penis, said tubular means having a first and second extremity, said first extremity sealingly engaging said first end of said collar means, said second extremity sealingly cooperating with the user's penis;

collection means sealingly cooperating with said second end of said collar means, the arrangement being such that in use of the device, the user's penis is sealingly supported by said tubular means so that the user's penis is disposed within said collar means; and said collection means including:

a tubular sleeve connected to said second end of said collar means.

3. The urinal device as set forth in claim 2 wherein:

said first portion and said second portion define therebetween an angle of substantially 90 degrees so that said portions together are of substantially capital "L" shaped cross sectional configuration.

4. The urinal device as set forth in claim 2 wherein:

said first portion is of open ended cylindrical configuration; said second portion extending from said first portion and being disposed approximately 90 degrees thereto for permitting the orientation of said collar means in any position thereof within the range 0–360 degrees relative to the user's penis so that the user thereof is able to sleep on either of the user's sides or on the user's back.

5. The urinal device as set forth in claim 4 wherein:

said second portion is rotatably received within said first portion for permitting rotation of said second portion relative to said first portion.

6. The urinal device as set forth in claim 2 wherein:

said first portion has a length of approximately 1.75 inches so that in use of the device, said first portion is disposed between said support means and the user's stomach such that said support means urges said first portion towards the user's stomach thereby inhibiting any tendency of the user's penis from retracting from within said first portion.

7. The urinal device as set forth in claim 2 wherein:

said collection means includes:

a tubular collection sleeve having a proximal and a distal end, said proximal end being sealingly secured to said second end of said collar means;

a valve disposed within said distal end for controllably draining said collection means.

8. The urinal device as set forth in claim 2 wherein:

said collection means includes:
- a tubular collection sleeve;
- a collection bag connected to said tubular sleeve such that said tubular sleeve is disposed between said collar means and said bag; and said tubular sleeve being fabricated from latex material.

9. The urinal device as set forth in claim 2 wherein:

said first and second portions are both of open ended cylindrical configuration, said first portion being coaxial relative to said second portion.

* * * * *